United States Patent
Adler

(10) Patent No.: US 8,054,553 B2
(45) Date of Patent: Nov. 8, 2011

(54) ILLUMINATION ANGLE CONTROL USING DICHROIC FILTERS

(75) Inventor: Avraham Adler, Nof Ayalon (IL)

(73) Assignee: Orbotech Ltd., Yavne (IL)

( * ) Notice: Subject to any disclaimer, the term of this patent is extended or adjusted under 35 U.S.C. 154(b) by 420 days.

(21) Appl. No.: 12/137,762

(22) Filed: Jun. 12, 2008

(65) Prior Publication Data

US 2009/0310239 A1    Dec. 17, 2009

(51) Int. Cl.
    G02B 27/14    (2006.01)
(52) U.S. Cl. .................. 359/634; 359/633
(58) Field of Classification Search ............ 359/634
    See application file for complete search history.

(56) References Cited

U.S. PATENT DOCUMENTS

| | | | |
|---|---|---|---|
| 3,085,468 A | 4/1963 | Hehn | |
| 4,552,441 A * | 11/1985 | Dewey | 353/31 |
| 5,268,788 A | 12/1993 | Fox et al. | |
| 5,359,192 A | 10/1994 | Williams et al. | |
| 6,033,087 A | 3/2000 | Shozo et al. | |
| 6,259,430 B1 * | 7/2001 | Riddle et al. | 345/589 |
| 6,501,075 B1 | 12/2002 | Trigiana | |
| 6,871,982 B2 | 3/2005 | Holman et al. | |
| 6,994,453 B2 | 2/2006 | Blanchard | |
| 7,237,909 B2 | 7/2007 | Yokote et al. | |
| 7,355,692 B2 | 4/2008 | Noy et al. | |
| 2002/0196450 A1 | 12/2002 | Olszak et al. | |
| 2004/0146295 A1 | 7/2004 | Furman et al. | |
| 2005/0030480 A1 | 2/2005 | Lippey et al. | |
| 2006/0007538 A1 | 1/2006 | Robinson | |
| 2007/0109528 A1 | 5/2007 | Caldwell et al. | |
| 2007/0133088 A1 | 6/2007 | Lippey et al. | |
| 2007/0138419 A1 * | 6/2007 | Bueno et al. | 250/586 |
| 2007/0206183 A1 | 9/2007 | Lebens et al. | |
| 2007/0211149 A1 | 9/2007 | Burtnyk et al. | |
| 2007/0236933 A1 | 10/2007 | Bierhuizen et al. | |
| 2008/0089052 A1 | 4/2008 | Katzir et al. | |

OTHER PUBLICATIONS

International Searching Authority, "International Search Report", "Written Opinion", and IPER issued in connection with International Patent Application No. PCT/IL2009/000545, dated Sep. 8, 2009.

* cited by examiner

Primary Examiner — Scott J Sugarman
Assistant Examiner — James C Jones
(74) Attorney, Agent, or Firm — Sughrue Mion, PLLC

(57) ABSTRACT

A method of controlling the illumination angle onto a target, including, illuminating onto the target with light from at least two light sources of pre-selected wavelengths; wherein each point on the target is illuminated by light from the light sources with a respective maximal illumination angle relative to a main illumination axis extending from substantially the center of the at least two light sources to the target, selecting a dichroic filter that transmits light from the at least two light sources as a function of the angle of incidence upon the filter, positioning the dichroic filter between the at least two light sources and the target to limit the transfer of light to light of the pre-selected wavelengths; and wherein the dichroic filter is selected to limit the maximal illumination angle illuminating each point on the target.

9 Claims, 7 Drawing Sheets

ILLUMINATION ANGLE CONTROL USING DICHROIC FILTERS

FIELD OF THE INVENTION

The present invention relates generally to control of the illumination angles of an object using dichroic filters.

BACKGROUND OF THE INVENTION

Many applications require illumination of points on a target at specific illumination angles to achieve a desired contrast for examining the surface, for example to analyze the surface of electrical circuits on a printed circuit board (PCB). Typically in process of fabrication of electrical circuits, such as printed circuit boards, interconnect devices, Integrated Circuits and flat panel displays, an automated optical inspection operation is used to identify defects in the electrical circuits or on the substrate. Typically examination of a PCB is achieved by illuminating the surface of the PCB line by line with one or more line light sources and scanning the line for analysis. A line light source may be created by various methods, for example by forming a row of glass fibers that originate from a point light source (e.g. a halogen light), or by forming a row of LED sources. A lens may be placed along the line between the line light source and the PCB to focus the light in the plane perpendicular to the line to achieve an optimal angle of illumination on each point along the line.

Along the longitudinal axis each point of the line on the PCB is illuminated from the multiple light sources forming the line light source. The overall angle of illumination of the point is determined by the dispersion angles of the point light sources that the line light source is made up from, for example a Halogen light source tends to generate light that spreads out forming an angle of about +/−25° from the focal point of the source along the longitudinal axis. LED light sources generally generate light that spreads out forming an angle of about 70° in all directions.

To optimally analyze a point on the PCB it is desired to illuminate the point symmetrically, to eliminate the need to perform calculations to compensate for the asymmetry of the lighting. However controlling the illumination angles of the points that make up the line light source in all directions constitutes a geometrical challenge for lens makers. Such a solution may be impossible or very costly depending on the size and number of points forming the line light source. Therefore other methods of controlling the dispersion angles of the light are desirable.

SUMMARY OF THE INVENTION

An aspect of an embodiment of the invention relates to a system and method for controlling the illumination angles of a beam of light from two or more points toward a line or area on a target by placing a dichroic filter between the light source and the illuminated target. The dichroic filter selectively transfers light depending on the wavelength and the angle of incidence of the light source. Selection of a dichroic filter that transfers a desired wavelength at specific angles of incidence enables the control of the resulting illumination beam upon the target.

In an exemplary embodiment of the invention, one or more rows of light sources are used to illuminate a line or area on a target. Optionally, a lens is used to focus the light in the direction perpendicular to the row of light sources, thus controlling the illumination angles for that direction. In some embodiments of the invention, each row illuminates a segment of the full angular coverage. In the direction parallel to the row of light sources the dichroic filter transfers specific wavelengths of light at specific ranges of angles of incidence upon the filter, so that the illumination angle in the parallel direction can also be limited. In some embodiments of the invention, the illumination angles on the target are the same in all directions. Alternatively, the light in the perpendicular direction may be focused using the lens to a narrower illumination angle than in the parallel direction using the dichroic filter. Optionally, if the lens focuses the light to a beam with a wider angle than provided by the dichroic filter, the filter will limit the illumination angle also in the perpendicular direction.

In some embodiments of the invention, the dichroic filter is placed parallel to the row of light sources, so that all of the light sources are handled symmetrically. Alternatively, the dichroic filter is placed at an angle relative to the row of light sources, so that some of the sources will transfer more light than others and for example to allow illumination from some light beams at obtuse angles relative to the row of light sources.

In some embodiments of the invention, the light beams illuminated from the light sources toward the target are transferred through more than one filter to enhance control of the illumination angles. Optionally, the dichroic filter may be a multi-band pass filter that supports more than one range of wavelengths that are transmitted through the filter if arriving at the filter at the designated range of angles supported by the filter.

There is thus provided according to an exemplary embodiment of the invention, a method of controlling the illumination angle onto a target, comprising:

illuminating onto the target with light from at least two light sources of pre-selected wavelengths; wherein each point on the target is illuminated by light from the light sources with a respective maximal illumination angle relative to a main illumination axis extending from substantially the center of the at least two light sources to the target;

selecting a dichroic filter that transmits light from the at least two light sources as a function of the angle of incidence upon the filter;

positioning the dichroic filter between the at least two light sources and the target to limit the transfer of light to light of the pre-selected wavelengths; and wherein the dichroic filter is selected to limit the maximal illumination angle illuminating each point on the target. Optionally, the dichroic filter is positioned perpendicular to the main illumination axis. Alternatively, the dichroic filter does not form a right angle relative to the main illumination axis.

In an exemplary embodiment of the invention, the angle of the dichroic filter is user controllable. Optionally, multiple dichroic filters are positioned sequentially along the main illumination axis. In an exemplary embodiment of the invention, the multiple dichroic filters are positioned at an angle relative to each other. Optionally, the dichroic filter is a multi pass filter. In an exemplary embodiment of the invention, the method further includes placing a lens between the at least two light sources and the target to focus the light from the at least two light sources onto the target along a first direction; and wherein the light illuminating the target along a second direction perpendicular to the first direction have substantially the same illumination angles as the first direction as a result of the positioning of the dichroic filter.

In an exemplary embodiment of the invention, the at least two light sources are provided in multiple rows of light sources parallel to each other and wherein the beams from each row of light sources is focused with a lens onto the target along a first direction, such that the combined beam that illuminates the target along the first direction has the same illumination angles as along a second direction perpendicular to the first direction as a result of the positioning of the dichroic filter. Optionally, each of the at least two light sources selectively provides light of multiple wavelengths and the controlled illumination angles differ for each wavelength.

There is further provided according to an exemplary embodiment of the invention, a system for controlling the illumination angle onto a target, comprising:

at least two light sources to illuminate the target;

a dichroic filter that transmits light from the at least two light sources as a function of the angle of incidence upon the filter; wherein the dichroic filter is positioned between the at least two light sources and the target;

wherein the light of the at least two light sources have pre-selected wavelengths;

wherein each point on the target is illuminated by light from the light sources with a respective maximal illumination angle relative to a main illumination axis extending from substantially the center of the at least two light sources to the target;

wherein the filter is selected to limit the maximal illumination angle illuminating each point on the target.

In an exemplary embodiment of the invention, the system further comprises a lens positioned between the at least two light sources and the target to focus the light from the at least two light sources onto the target along a first direction; and wherein the light illuminating the target along a second direction perpendicular to the first direction have substantially the same illumination angles as the first direction as a result of positioning the dichroic filter between the target and the at least two light sources.

There is further provided according to an exemplary embodiment of the invention, an illumination device for illuminating a target, comprising:

one or more rows of light sources, wherein each light source provides light of one or more wavelengths;

a lens parallel to each row of light sources to focus the light from the rows of light sources so that the combined light beam that illuminates the target has a specific angle relative to a main illumination axis extending from substantially the center of the at least two light sources to the target;

a dichroic filter placed between the target and the lens that transmits specific light wavelengths incident on the filter at a specific range of angles, such that the resulting illumination angles for at least one wavelength, on the target along the direction perpendicular to the row of light sources is symmetrical with the illumination angles along the direction parallel to the row of light sources.

Optionally, the system includes multiple dichroic filters. In an exemplary embodiment of the invention, the resulting illumination angles on the target along the direction perpendicular to the row of light sources is symmetrical with the illumination angles along the direction parallel to the row of light sources for a single wavelength. Optionally, the resulting illumination angles on the target along the direction perpendicular to the row of light sources is symmetrical with the illumination angles along the direction parallel to the row of light sources for more than one wavelength.

BRIEF DESCRIPTION OF THE DRAWINGS

The present invention will be understood and appreciated more fully from the following detailed description taken in conjunction with the drawings. Identical structures, elements or parts, which appear in more than one figure, are generally labeled with a same or similar number in all the figures in which they appear, wherein.

DETAILED DESCRIPTION OF THE INVENTION

Figure 1:
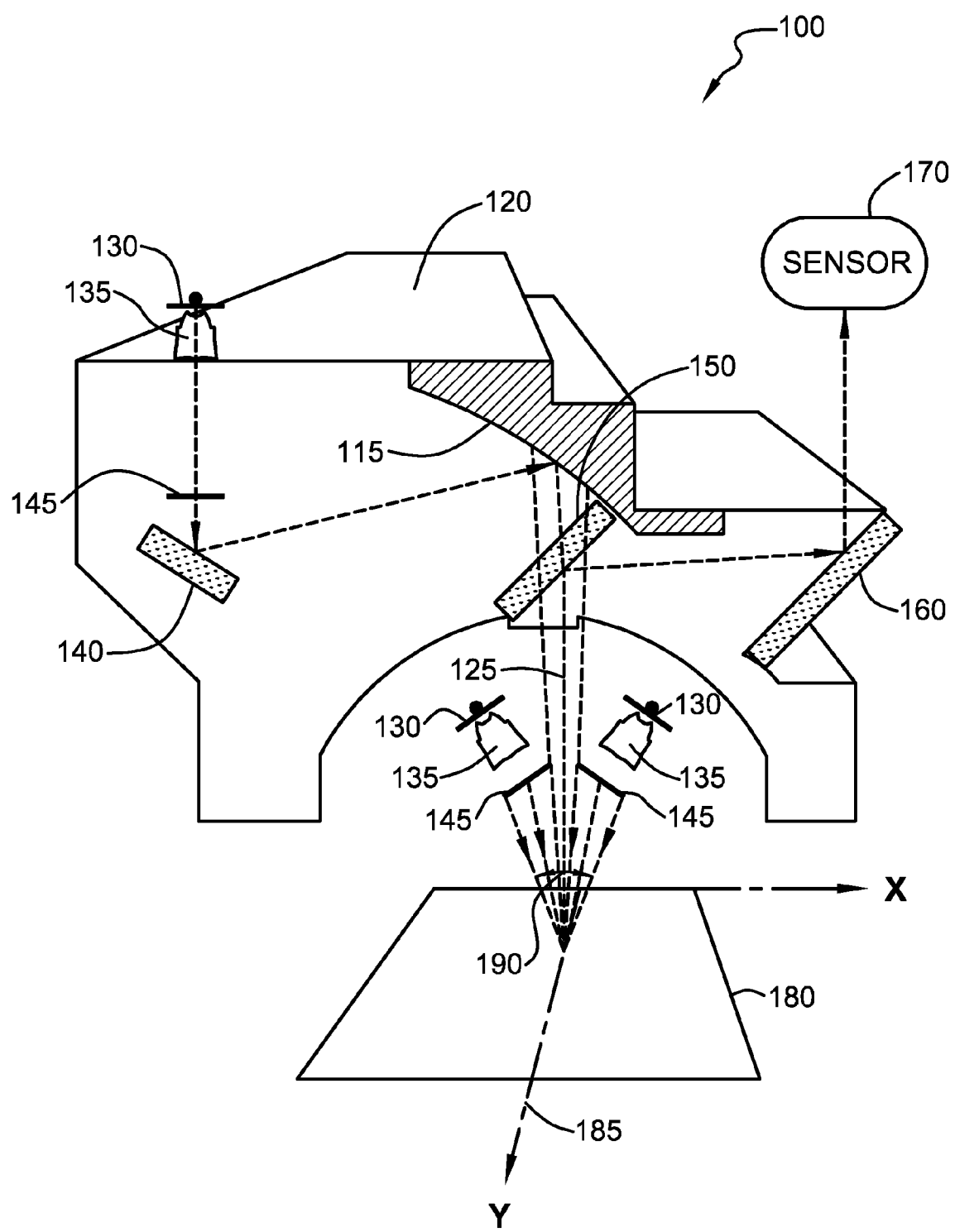
FIG. 1 is a schematic illustration of a cross sectional view of a device for optically analyzing electrical circuits, according to an exemplary embodiment of the invention.

FIG. 1 is a schematic illustration of a cross sectional view of a device 100 for optically analyzing electrical circuits, for example as manufactured on a PCB or other surface, according to an exemplary embodiment of the invention. Optionally, device 100 includes a base 120 to mount optical elements for controlling illumination onto a target 180 and sampling reflection from target 180. In an exemplary embodiment of the invention, three line light sources 130 are mounted on base 120 to illuminate target 180. Optionally, target 180 is made up from a material that serves as a Lambertian surface selectively coated with a metallic conductor based on a circuit design. Typically, the Lambertian surface and the metallic conductor have different levels of reflection so that by sampling light reflected from target 180 the circuit manufacture can be verified, for example by detecting manufacturing errors.

In an exemplary embodiment of the invention, a light signal 125 is formed by the reflectance of light sources 130 from target 180. Light signal 125 is reflected toward a semi-transparent mirror 150 that passes light signal 125 on through a mirror 160 and/or through any other optical path toward a sensor 170. Sensor 170 may be for example a CCD (Charged Coupled Device), a CMOS (Complementary Metal Oxide Semiconductor), a photomultiplier or any other adequate sensor. In an exemplary embodiment of the invention, sensor 170 samples light signal 125 and provides the sample as digitized information to a computer to analyze target 180 by comparing it to the circuit design. Alternatively or additionally other methods known in the art can be used in performing Automatic Optical Inspection (AOI) of electrical circuits.

In some embodiments of the invention, three light sources 130 are used to illuminate a line 185 on the target, for example the first light source 130 may be positioned to illuminate from one side of line 185, the second light source 130 may be positioned to illuminate from the opposite side of line 185 and the third light source 130 may be positioned to illuminate from directly above line 185. In some embodiments of the invention, a greater number of light sources may be used (e.g. 4, or 5 or more) or a smaller number of light sources may be used (e.g. 1, or 2). Optionally, a lens 135 is placed in the path of the light toward line 185 to focus the light from light sources 130 so that the combined light incident onto line 185 illuminates the line at a predetermined angle 190 (e.g. 30°, 55°, or 100°) in a plane parallel to the X coordinate as shown in FIG. 1. In some embodiments of the invention, each light source 130 contributes by illuminating over the entire angle 190. Alternatively, each light source 130 contributes a segment of angle 190. In an exemplary embodiment of the invention, a dichroic filter 145 is placed in the light path, for example after lens 135 to control the angle by which each point of line 185 will be illuminated in the Y direction as described below. In some embodiments of the invention, the position of the optical elements may vary, for example dichroic filter 145 may be placed before lens 135. Optionally, some of the light paths may be more complex and some may be less complex, for example the center light source in FIG. 1 is not placed along the same arc as the other two light sources, but instead is positioned remotely and transferred through a mirror 140, a curved mirror 115 and a semi-transparent mirror 150, to allow the reflected light to be returned in the same direction via semi-transparent mirror 150.

It should be noted that the light source for implementing the invention is not limited to a point light source or a line light source as generally used in this description. Optionally, other types of light sources (e.g. a multiline source an area source, or other variations) may also be used and the details described herein are equally applicable to these cases.

Additionally, it should be noted that the invention is not limited to a specific type of electronic circuit or a specific type of surface serving as the target on which an electronic circuit is manufactured, for example the electronic circuit may be implemented as printed circuit boards, interconnected devices, Integrated Circuits, flat panel displays and any other form of electronic circuits or surfaces. Likewise, the invention is not limited to electronic circuits and is equally applicable to other types of targets.

Figure 2A:
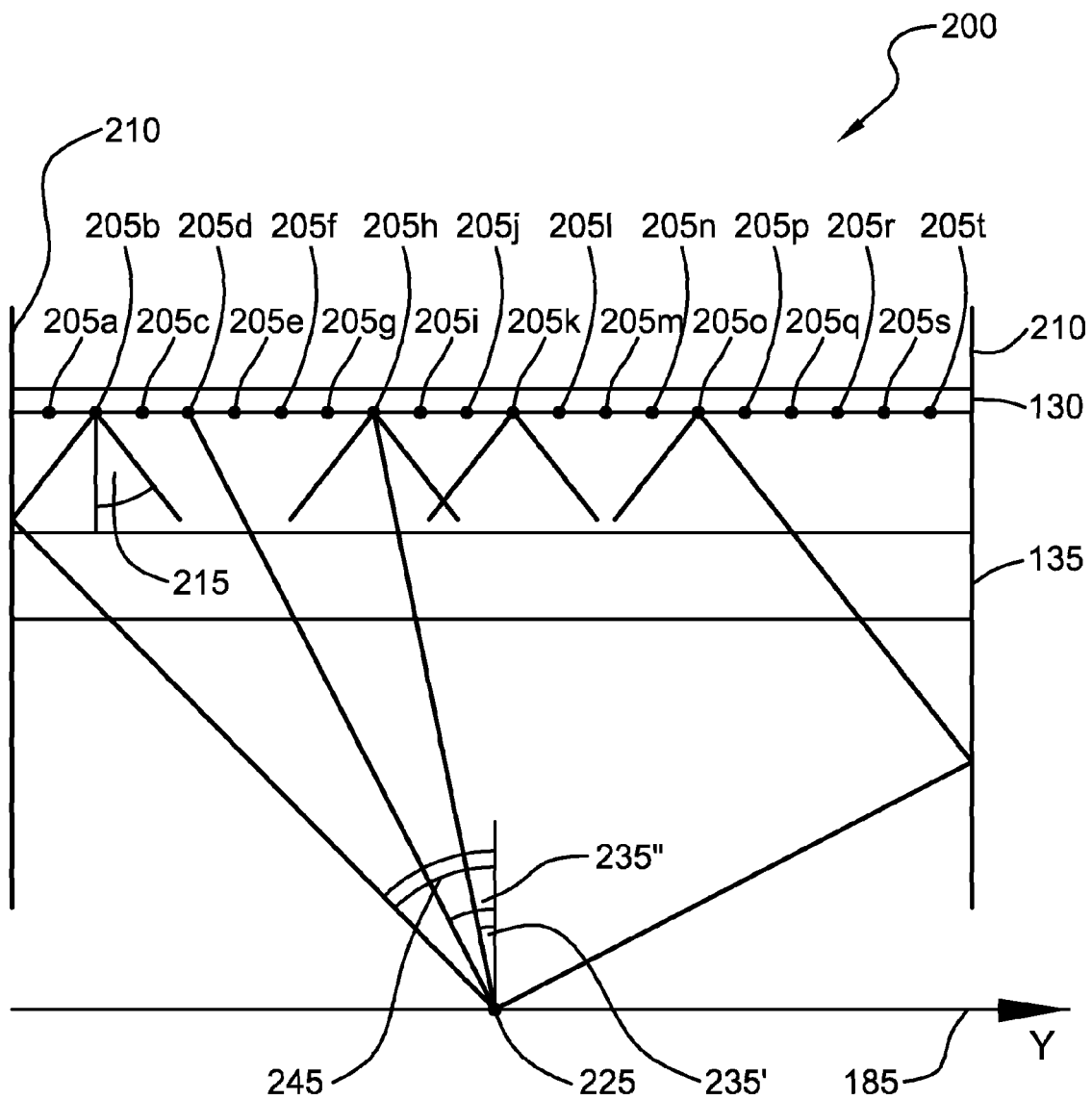
FIGS. 2A and 2B are schematic illustrations of a side view of illumination of a point on a target along the longitudinal axis with and without use of a dichroic filter respectively, according to an exemplary embodiment of the invention.
Figure 2B:
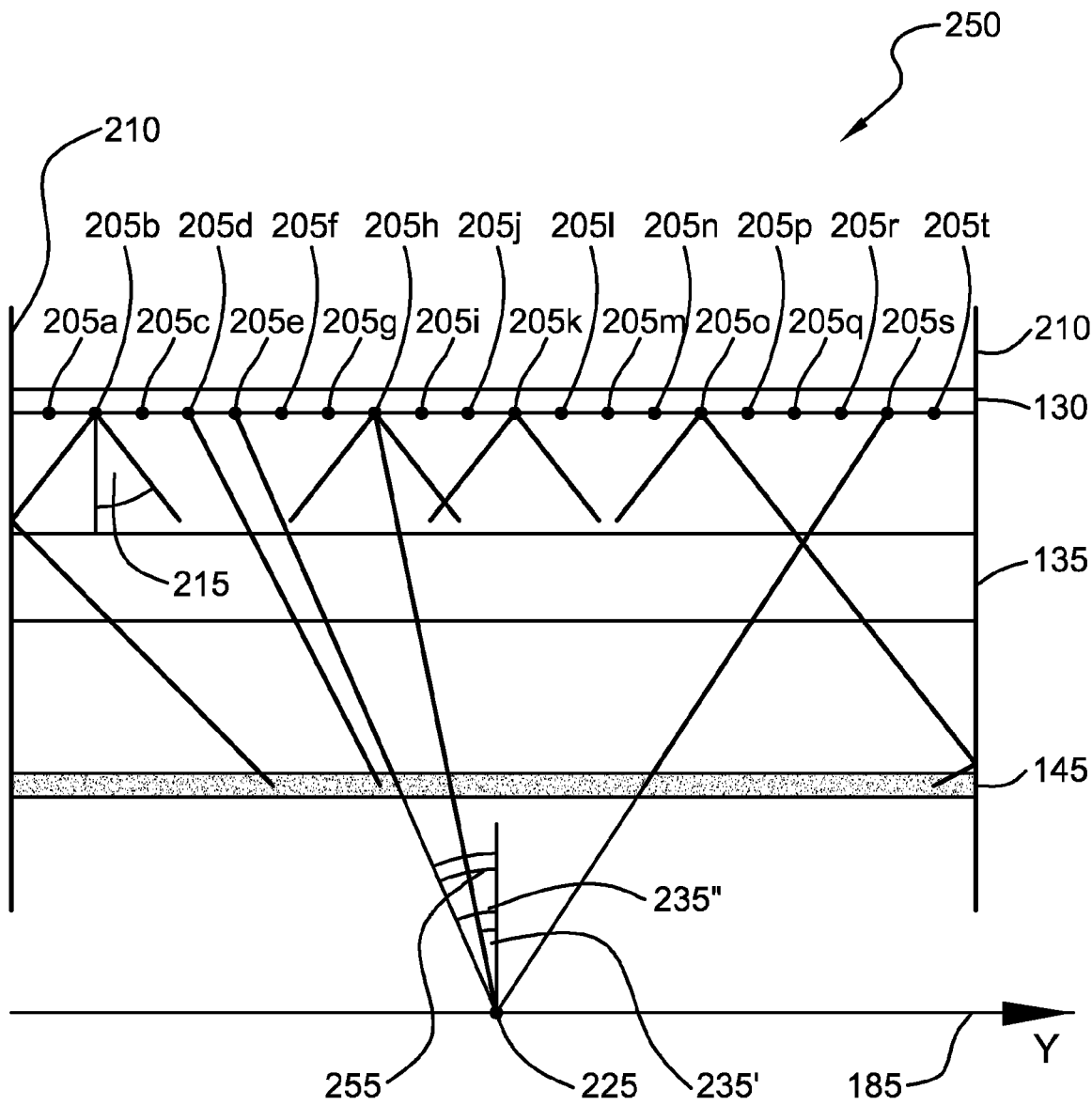

FIG. 2A is a schematic illustration of a side view 200 of illumination of a point 225 on a target along the longitudinal axis (Y) without use of a dichroic filter, and FIG. 2B is a schematic illustration of a side view 250 of illumination of a point 225 on a target along the longitudinal axis (Y) using a dichroic filter 145, according to an exemplary embodiment of the invention. In an exemplary embodiment of the invention, in the X direction all the light is collected together toward a line parallel to Y axis 185 by lens 135 and directed to form a narrow intense illumination line limited by the desired illumination angle. Optionally, in the Y direction each light point 205 contributes to the illumination of point 225 if the dispersion of the light point covers the point. In an exemplary embodiment of the invention, light source 130 is made up from a line of light points $205_a$-$205_t$ (e.g. LEDs, fibers). Optionally, each point produces a light beam which spreads out by an angle 215 (e.g. 70°) relative to the normal to light source 130, the angle depending on the properties of the light source. In an exemplary embodiment of the invention, the light passes through lens 135 towards point 225. Optionally, the sides of base 120 are coated to form a highly reflective mirror 210 (e.g. 96% reflectance) so that the light source line can be viewed as almost infinite by points 225 and each point 225 is illuminated by many light points 205 of the line light source 130. In FIG. 2A, light points $205_a$-$205_t$ illuminate the specific point 225, each of those points illuminate point 225 with a different angle 235 (e.g. 235' and 235"), directly or indirectly via mirror 210, up to the maximum angle 245 that is equal to angle 215. FIG. 2A shows specifically illumination lines from some of lights points $205_a$-$205_f$, however it should be understood that all the points contribute and only some are shown to enhance clarity. In FIG. 2B a dichroic filter 145 is placed after lens 135 to limit the effective illumination angle along the longitudinal (Y) axis, so that the resulting illumination angles on point 225 will be optimal for the application desired, for example limiting illumination of point 225 up to angle 255 instead of angle 245 (angle 255≦angle 245) without filter 145. In an exemplary embodiment of the invention, the decreasing of intensity up to angle 255 is not uniform and optionally has a slow slope so point 225 is illuminated at a higher intensity at angle 235 than at angle 255.

Figure 3A:
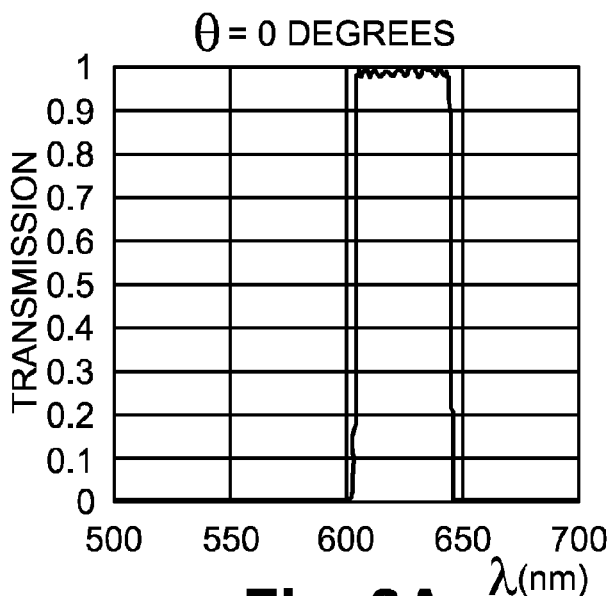
FIGS. 3A-3C are schematic illustrations of a dichroic filter transmission spectrum as a function of the angle of incidence, according to an exemplary embodiment of the invention.
Figure 3B:
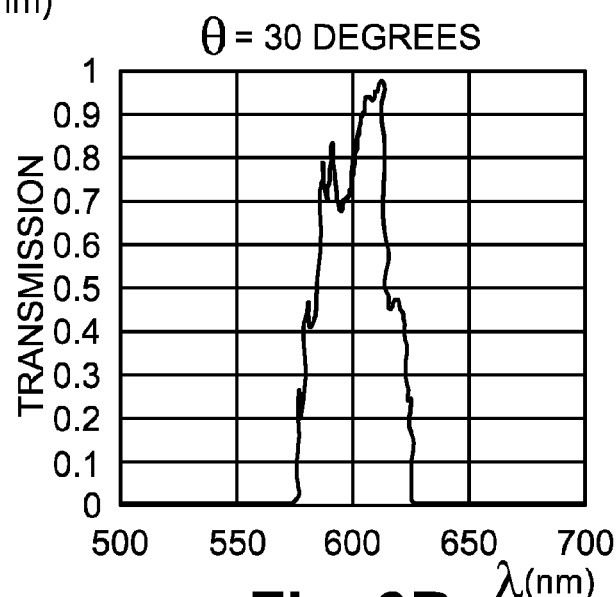
Figure 3C:
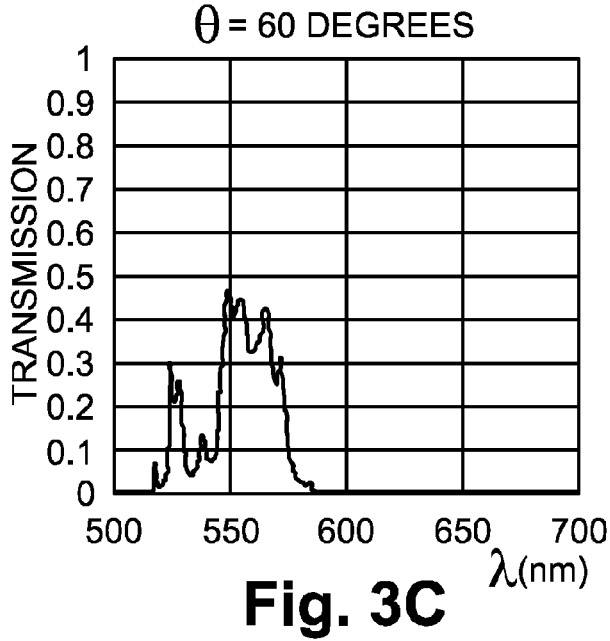

A light ray originating from a light point 205 is incident on dichroic filter 145 at an angle 235 relative to the normal to the filter. FIGS. 3A-3C are schematic illustrations of the transmitted spectrum of dichroic filter 145 for different angles of incidence 235, according to an exemplary embodiment of the invention. As shown by FIGS. 3A-3C, for a specific wavelength (λ in nanometers (nm)), at certain angles the dichroic filter transmits most of the light (e.g. more than 60% or 70%) and at certain angles the light is reflected and only a small percent is transmitted (e.g. less than 20% or 30%). The transmission of the specific wavelength at an angle θ is equal to the transmission of a different wavelength at normal incidence. The ratio between the wavelengths (in air) is given by:

$$\frac{\lambda_\theta}{\lambda_0} = \sqrt{1 - \frac{\sin^2\theta}{(N^*)^2}}$$

Wherein
 θ=Angle of incidence.
 $\lambda_\theta$=wavelength at angle of incidence.
 $\lambda_0$=wavelength at normal incidence with same transmission.
 N*=Effective refractive index of the filter.

In an exemplary embodiment of the invention, light point 205 produces light with a specific wavelength or a specific range of wavelengths. Optionally, dichroic filter 145 is selected to match the light waves illuminated by light point 205 such that the resulting angles illuminating point 225 will be reduced relative to the original angle forming the beam produced by light point 205. As shown in FIGS. 3A-3C when light point 205 produces a reddish light beam with a wavelength of about 630 nm, the rays that are incident upon dichroic filter 145 at an angle of 0° (e.g. FIG. 3A) will be almost completely (e.g. 96%) transmitted through the filter. For light rays that are incident upon dichroic filter 145 at an angle of 30°, only about 80% (e.g. FIG. 3B) will be transmitted. Light rays that are incident upon dichroic filter 145 at an angle of 60° (e.g. FIG. 3C) will be essentially reflected and not transmitted. Thus by selecting or producing a dichroic filter to match the wavelengths of the light produced by light points 205, the angle of incidence on point 225 can be controlled to achieve symmetrical illumination from all sides of point 225.

In some embodiments of the invention, a dual-band or multi-band dichroic filter (e.g. SEMROCK FF01-468/624-25) is used so that more than one wavelength can be provided by light point 205 and have its illumination angle controlled by the use of dichroic filter 145. Optionally, each light point 205 may comprise multiple LEDs illuminating light of different wavelengths or each light point 205 may provide light of a different wavelength (e.g. using a Lambertian LED, or fibers). In some embodiments of the invention, target 180 may be illuminated by light of one wavelength or of multiple wavelengths. Optionally, dichroic filter 145 may be selected such that each wavelength illuminates point 225 on line 185 with different maximal angles.

Figure 4:
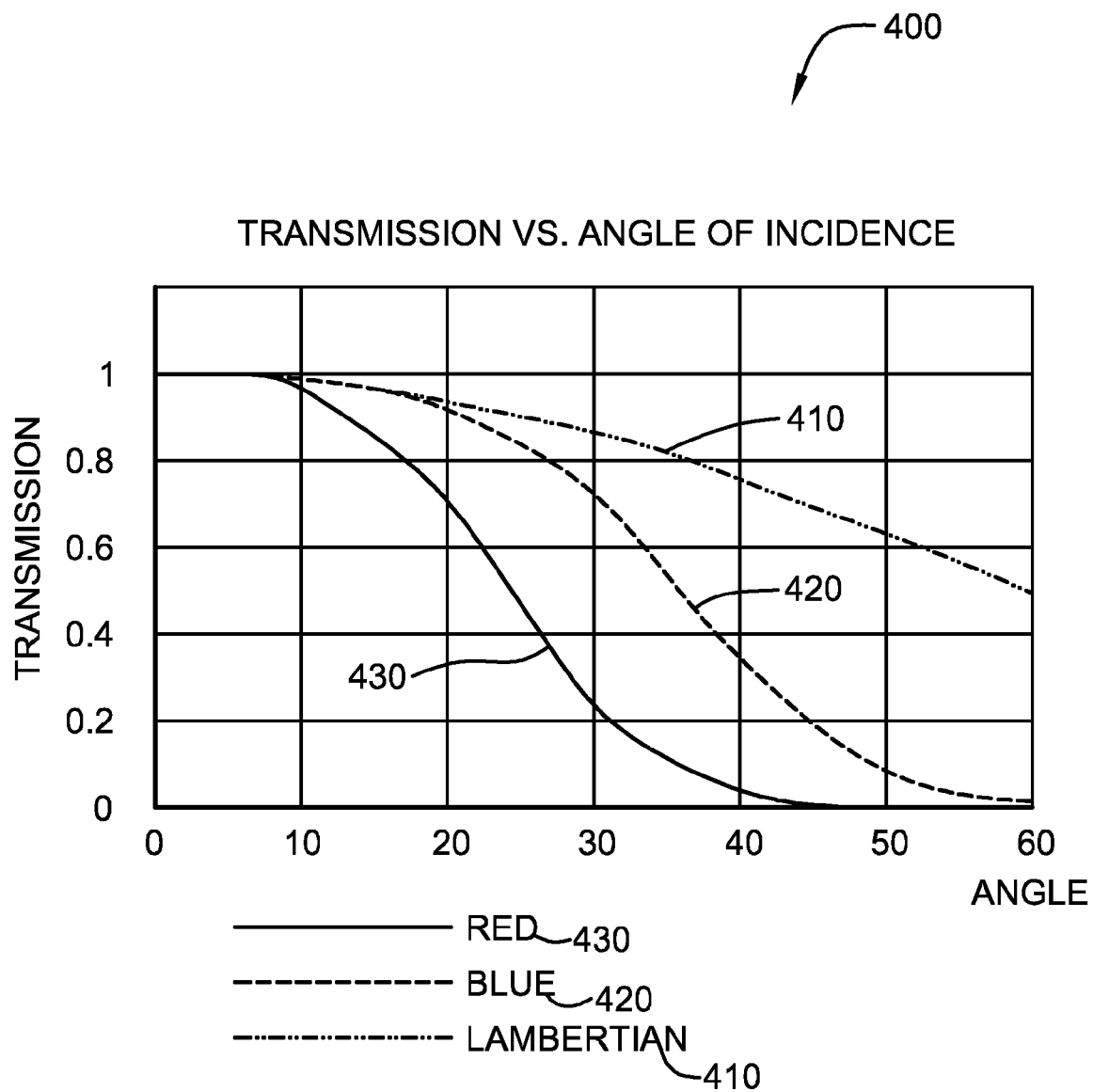
FIG. 4 is a schematic illustration of a graph of transmission versus the angle of incidence through a dichroic filter, according to an exemplary embodiment of the invention.

FIG. 4 is a schematic illustration of a graph 400 of transmission versus the angle of incidence through a dichroic filter, according to an exemplary embodiment of the invention. Line 410 illustrates a transmitted light beam produced for example by a Lambertian LED. Optionally, the beam is directed toward a dual band pass filter (e.g. SEMROCK FF01-468/624-25). The normalized transmission of the filter is illustrated by lines 420 and 430. Line 420 represents a light beam with a central wavelength of 460 nm (blue light) and line 430 represents a light beam with a central wavelength of 630 nm (red light) as the wavelengths that are transmitted by the filter. Between 0° to about 20° most of the two wavelengths are transmitted. However as the angle of incidence relative to the normal increases the transmission diminishes, and at angles above 40°-50° almost no light is transmitted.

Figure 5:
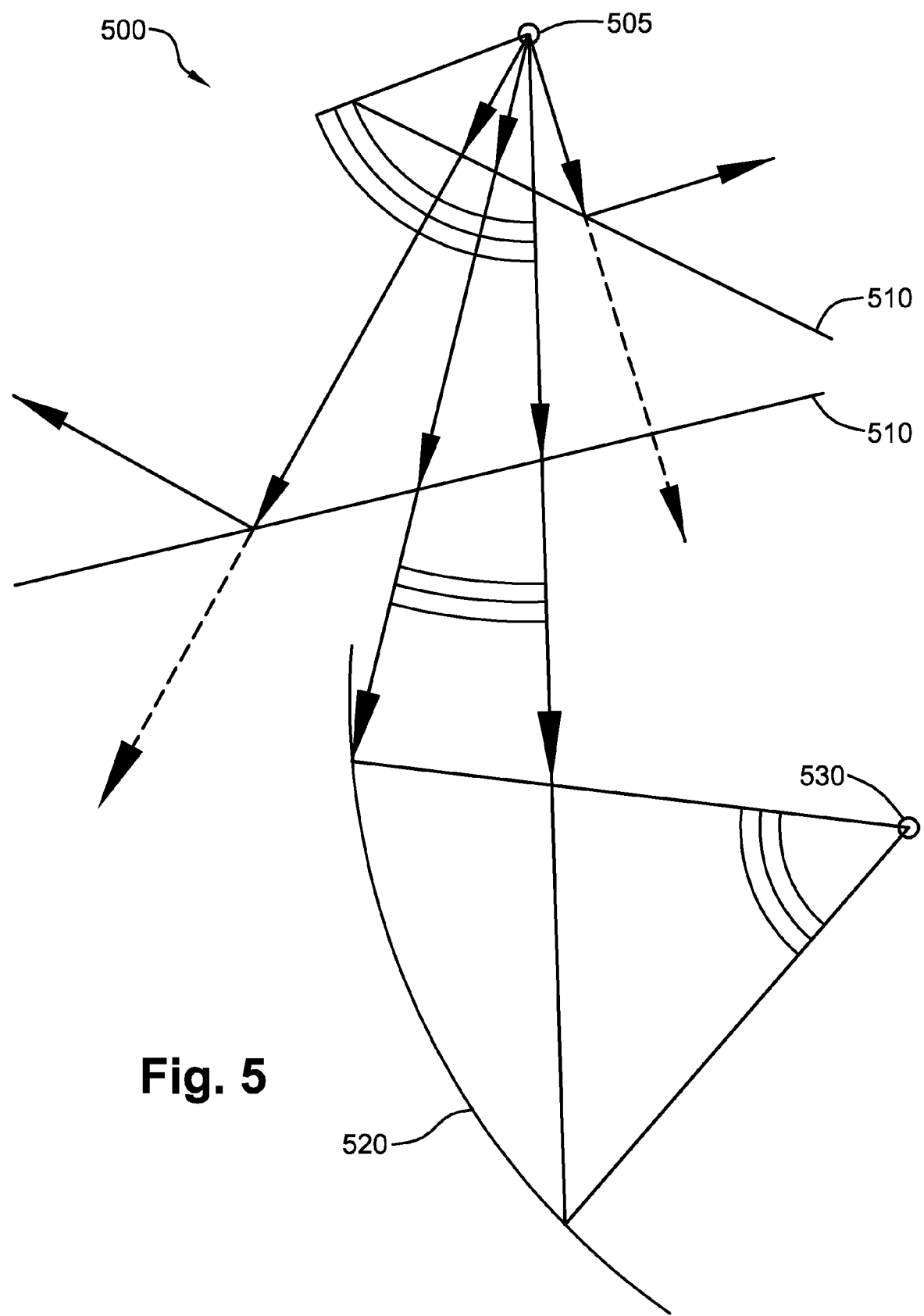
FIG. 5 is a schematic illustration of the use of two tilted dichroic filters and a mirror to transfer specific light rays from a light source and to block others thus controlling the angles by which a target is illuminated, according to an exemplary embodiment of the invention.

In an exemplary embodiment of the invention, by selecting a single dichroic filter and the light wavelength used the angle of illuminating point 225 is determined. Alternatively or additionally, two or more dichroic filters 145 may be placed in series or in parallel at various angles relative to each other to further control the illumination angle and the strength of the light beam illuminating point 225, for example to transfer light from large angles of incidence or to asymmetrically illuminate a point. FIG. 5 is a schematic illustration 500 of the use of two tilted dichroic filters 510 and a mirror 520 to transfer specific light rays from a light source 505 and to block others thus controlling the angles by which a target 530 is illuminated. In an exemplary embodiment of the invention, the illumination angle may be shifted, further limited or expanded, for example to provide maximum illumination on a target at angles between 20°-50° instead of 0° to 30°. Optionally, dichroic filters 510 may be movable, for example controlled by a motor to allow user control of the light being illuminated upon a target.

Figure 6A:
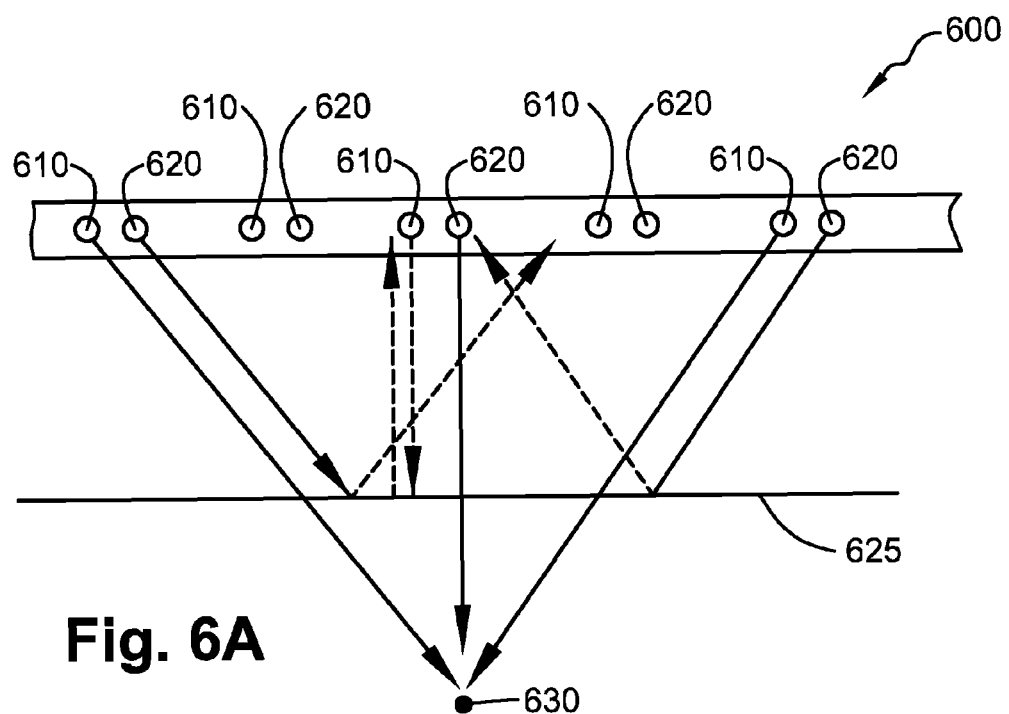
FIG. 6A is a schematic illustration of a line light source, wherein each point on the line is made up from two light points of different wavelengths, according to an exemplary embodiment of the invention.

FIG. 6A is a schematic illustration of a line light source 600 wherein each point of the line is made up from two light points 610, 620 of different wavelengths, according to an exemplary embodiment of the invention. Optionally, light from light source 600 is transmitted through a multi band dichroic filter 625 that responds differently for each wavelength, such that each range of angles provides light of a different wavelength. Optionally, by controlling the intensity of each light source, the illumination angle toward a target 630 can be controlled.

Figure 6B:
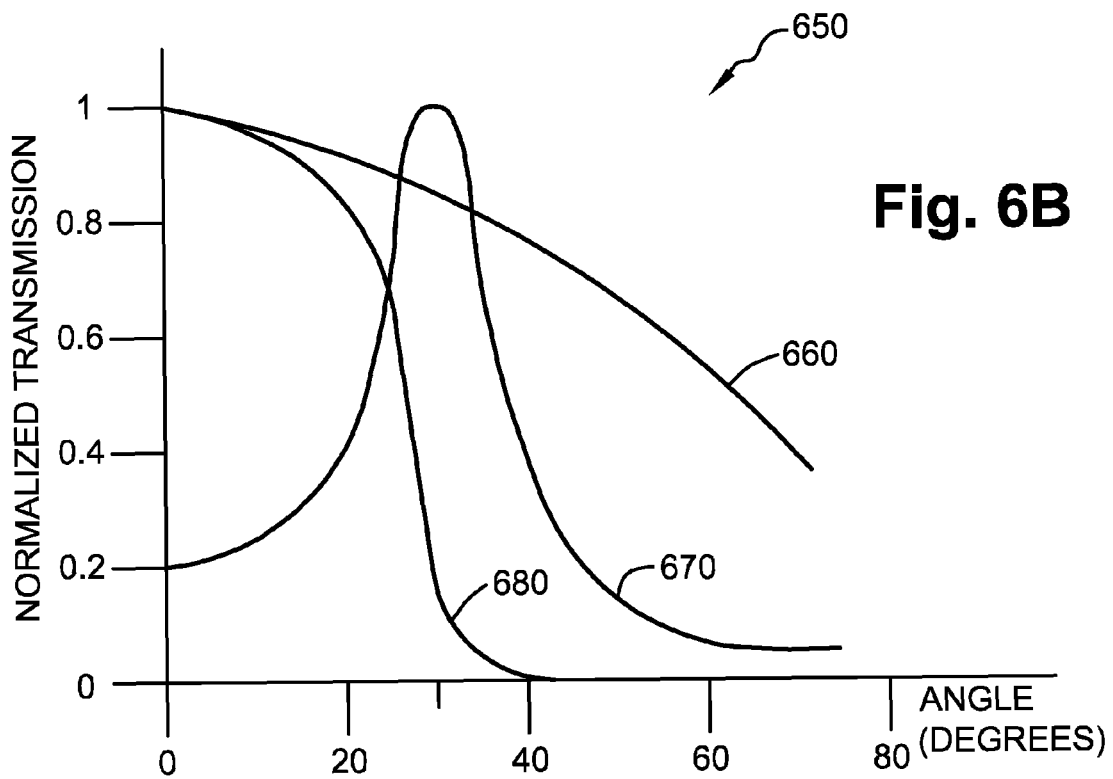
FIG. 6B is a schematic illustration of a graph showing transmission versus the angle of incidence using two light points of different wavelengths, according to an exemplary embodiment of the invention.

FIG. 6B is a schematic illustration of a graph 650 showing transmission versus the angle of incidence using two light points (610, 620) of different wavelengths, according to an exemplary embodiment of the invention. Optionally, line 660 shows the transmission of a Lambertian light source. Line 670 shows the transmission of a LED with a wavelength of 590 nm, and line 680 shows the transmission of a LED with a wavelength of 620 nm. According to the case depicted by graph 650 most of the intensity of the light illuminating target 630 up to an angle of about 25° from the normal will be contributed by the 620 nm LED. Most of the intensity at angles above 25° until about 60° is contributed by the 590 nm LED. In an exemplary embodiment of the invention, the use of multiple wavelengths may enhance analysis of surfaces that respond differently to different wavelengths.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the invention. Further combinations of the above features are also considered to be within the scope of some embodiments of the invention.

Section headings are provided for assistance in navigation and should not be considered as necessarily limiting the contents of the section.

It will be appreciated by persons skilled in the art that the present invention is not limited to what has been particularly shown and described hereinabove. Rather the scope of the present invention is defined only by the claims, which follow.

The invention claimed is:

1. A method of controlling the illumination angle onto a target, comprising:
   illuminating onto the target with light from at least two light sources of pre-selected wavelengths; wherein each point on the target is illuminated by light from the light sources with a respective maximal illumination angle relative to a main illumination axis extending from substantially the center of the at least two light sources to the target;
   selecting a dichroic filter that transmits light from the at least two light sources as a function of the angle of incidence upon the filter; and
   positioning the dichroic filter between the at least two light sources and the target to limit the transfer of light to light of the pre-selected wavelengths;
   wherein said dichroic filter is selected to limit the maximal illumination angle illuminating each point on the target;
   wherein said dichroic filter does not form a right angle relative to the main illumination axis; and
   wherein the angle of the dichroic filter is user controllable.

2. A method of controlling the illumination angle onto a target, comprising:
   illuminating onto the target with light from at least two light sources of pre-selected wavelengths; wherein each point on the target is illuminated by light from the light sources with a respective maximal illumination angle relative to a main illumination axis extending from substantially the center of the at least two light sources to the target;
   selecting a dichroic filter that transmits light from the at least two light sources as a function of the angle of incidence upon the filter; and
   positioning the dichroic filter between the at least two light sources and the target to limit the transfer of light to light of the pre-selected wavelengths;
   wherein said dichroic filter is selected to limit the maximal illumination angle illuminating each point on the target; and
   further comprising placing a lens between the at least two light sources and the target to focus the light from the at least two light sources onto the target along a first direction; and
   wherein the light illuminating the target along a second direction perpendicular to the first direction have substantially the same illumination angles as the first direction as a result of the positioning of the dichroic filter.

3. A method of controlling the illumination angle onto a target, comprising:
   illuminating onto the target with light from at least two light sources of pre-selected wavelengths; wherein each point on the target is illuminated by light from the light sources with a respective maximal illumination angle relative to a main illumination axis extending from substantially the center of the at least two light sources to the target;

selecting a dichroic filter that transmits light from the at least two light sources as a function of the angle of incidence upon the filter; and positioning the dichroic filter between the at least two light sources and the target to limit the transfer of light to light of the pre-selected wavelengths;

wherein said dichroic filter is selected to limit the maximal illumination angle illuminating each point on the target; and wherein said at least two light sources are provided in multiple rows of light sources parallel to each other and wherein the beams from each row of light sources is focused with a lens onto the target along a first direction, such that the combined beam that illuminates the target along the first direction has the same illumination angles as along a second direction perpendicular to the first direction as a result of the positioning of the dichroic filter.

4. A method of controlling the illumination angle onto a target, comprising:

illuminating onto the target with light from at least two light sources of pre-selected wavelengths; wherein each point on the target is illuminated by light from the light sources with a respective maximal illumination angle relative to a main illumination axis extending from substantially the center of the at least two light sources to the target;

selecting a dichroic filter that transmits light from the at least two light sources as a function of the angle of incidence upon the filter; and positioning the dichroic filter between the at least two light sources and the target to limit the transfer of light to light of the pre-selected wavelengths;

wherein said dichroic filter is selected to limit the maximal illumination angle illuminating each point on the target; and wherein each of the at least two light sources selectively provides light of multiple wavelengths and the controlled illumination angles differ for each wavelength.

5. A system for controlling the illumination angle onto a target, comprising:

at least two light sources to illuminate the target;

a dichroic filter that transmits light from the at least two light sources as a function of the angle of incidence upon the filter; wherein the dichroic filter is positioned between the at least two light sources and the target;

wherein the light of the at least two light sources have pre-selected wavelengths;

wherein each point on the target is illuminated by light from the light sources with a respective maximal illumination angle relative to a main illumination axis extending from substantially the center of the at least two light sources to the target;

wherein said filter is selected to limit the maximal illumination angle illuminating each point on the target; and further comprising a lens positioned between the at least two light sources and the target to focus the light from the at least two light sources onto the target along a first direction; and wherein the light illuminating the target along a second direction perpendicular to the first direction have substantially the same illumination angles as the first direction as a result of positioning the dichroic filter between the target and the at least two light sources.

6. An illumination device for illuminating a target, comprising:

one or more rows of light sources, wherein each light source provides light of one or more wavelengths;

a lens parallel to each row of light sources to focus the light from the rows of light sources so that the combined light beam that illuminates the target has a specific angle relative to a main illumination axis extending from substantially the center of the at least two light sources to the target;

a dichroic filter placed between the target and the lens that transmits specific light wavelengths incident on the filter at a specific range of angles, such that the resulting illumination angles for at least one wavelength, on the target along the direction perpendicular to the row of light sources is symmetrical with the illumination angles along the direction parallel to the row of light sources.

7. A system according to claim 6, further comprising multiple dichroic filters.

8. A system according to claim 6, wherein the resulting illumination angles on the target along the direction perpendicular to the row of light sources is symmetrical with the illumination angles along the direction parallel to the row of light sources for a single wavelength.

9. A system according to claim 6, wherein the resulting illumination angles on the target along the direction perpendicular to the row of light sources is symmetrical with the illumination angles along the direction parallel to the row of light sources for more than one wavelength.

* * * * *